US00PP10195P

United States Patent [19]

Wain

[11] Patent Number: Plant 10,195

[45] Date of Patent: Jan. 13, 1998

[54] CHRYSANTHEMUM PLANT NAMED 'SKYLARK'

[75] Inventor: Peter Wain, Portsmouth, United Kingdom

[73] Assignee: Cleangro Limited, Chichester, United Kingdom

[21] Appl. No.: 751,867

[22] Filed: Nov. 18, 1996

[51] Int. Cl.[6] ..... A01H 5/00

[52] U.S. Cl. ..... Plt./76

[58] Field of Search ..... Plt./76, 80

*Primary Examiner*—Howard J. Locker
*Attorney, Agent, or Firm*—C. A. Whealy

[57] ABSTRACT

A distinct cultivar of Chrysanthemum plant named 'Skylark', characterized by its upright and compact plant habit; slow growth rate; large decorative-type inflorescences; lavender ray florets; numerous ray florets per inflorescence; and good garden performance.

2 Drawing Sheets

The present invention relates to a new and distinct cultivar of garden Chrysanthemum plant, botanically known as *Dendranthema grandiflora* and referred to by the cultivar name Skylark.

The new cultivar is a product of a planned breeding program conducted by the inventor in Chichester, West Sussex, United Kingdom. The objective of the breeding program was to create new garden Chrysanthemum cultivars having desirable inflorescence colors and good garden performance.

The new cultivar originated from a cross made by the inventor of the proprietary selection 7/GM/94 as the female, or seed, parent with the commercial cultivar Lynn (U.S. Plant Pat. No. 8,171) as the male, or pollen, parent.

The new Chrysanthemum was discovered and selected by the inventor as a flowering plant within the progeny of the stated cross in a controlled environment in Chichester, West Sussex, United Kingdom.

Asexual reproduction of the new cultivar by terminal cuttings taken at Chichester, West Sussex, United Kingdom, has shown that the unique features of this new Chrysanthemum are stable and reproduced true to type in successive generations.

The following traits have been repeatedly observed and are determined to be the unique characteristics of 'Skylark'. These characteristics in combination distinguish 'Skylark' as a new and distinct cultivar:

1. Upright and compact plant habit, slow growth rate.
2. Large decorative-type inflorescences.
3. Lavender ray florets.
4. Numerous ray florets per inflorescence.
5. Good garden performance.

The cultivar Skylark has not been observed under all possible environmental conditions. The phenotype may vary somewhat with variations in environment such as temperature, daylength and light intensity, without, however, any variance in genotype.

In side-by-side comparisons in Chichester, West Sussex, United Kingdom, under commercial practice, plants of the new Chrysanthemum have more ray florets, differ in ray floret color and flower later than plants of the female parent, the proprietary selection 7/GM/94. In the same comparisons, plants of the new Chrysanthemum are more open and upright in plant habit, have slightly larger inflorescences, fewer inflorescences and flower earlier than plants of the cultivar Lynn. In addition, plants of the new Chrysanthemum have darker ray florets than plants of the cultivar Lynn.

Plants of the new Chrysanthemum can be compared to the cultivar Debonair (U.S. Plant Pat. No. 5,324). However, in side-by-side comparisons conducted in Oxnard, Calif., under commercial practice, plants of the new Chrysanthemum differed from plants of the cultivar Debonair in the following characteristics:

1. Plants of the new Chrysanthemum are shorter, more compact and slower in growth rate than plants of the cultivar Debonair.
2. Plants of the new Chrysanthemum are not as freely branching as plants of the cultivar Debonair.
3. Leaves of plants of the new Chrysanthemum have three lobes whereas leaves of plants of the cultivar Debonair have five lobes.
4. Plants of the new Chrysanthemum have larger but fewer inflorescences than plants of the cultivar Debonair.
5. Ray floret color of plants of the new Chrysanthemum is slightly lighter than ray floret color of plants of the cultivar Debonair.
6. Plants of the new Chrysanthemum have longer peduncles than plants of the cultivar Debonair.

A detailed comparison of plants of the new Chrysanthemum and the cultivar Debonair appears in Chart A at the end of the specification.

The accompanying colored photographs illustrate the overall appearance of the new cultivar, showing the colors as true as it is reasonably possible to obtain in colored reproductions of this type.

The first photograph comprises a side perspective view of a typical flowering 16.5-cm container of 'Skylark' with one cutting in the container.

The second photograph comprises a close-up view of four leaves at different stages of development and a fully opened inflorescence. Foliage and floret colors in the photographs may appear different from the actual colors due to light reflectance.

In the following description, color references are made to The Royal Horticultural Society Colour Chart except where general terms of ordinary dictionary significance are used. The following observations and measurements describe plants grown in Oxnard, Calif., under commercial practice in a glass-covered greenhouse with average night temperatures of 18° C., average day temperatures of 30° C., and light levels of 2,000 (cloudy conditions) to 9,000 (sunny conditions) footcandles.

After sticking unrooted cuttings of the new cultivar, plants received 4 weeks of long day/short nights followed by short day/long nights until flowering. Measurements and numerical values represent ranges or averages for six typical flowering plants.

anical classification: *Dendranthema grandiflora* cultivar 'Skylark'.

nmercial classification: Garden Chrysanthemum.

ntage:

*Female, or seed, parent.*—*Dendranthema grandiflora* proprietary selection 7/GM/94.

*Male, or pollen, parent.*—*Dendranthema grandiflora* commercial cultivar Lynn (U.S. Plant Pat. No. 8,171).

pagation:

*Type.*—Terminal tip cuttings.

*Time to rooting.*—10 to 12 days with soil temperatures of 20C.

*Rooting habit.*—Fine, fibrous and well-branched.

nt Description:

*Appearance.*—Perennial herbaceous garden plant. Upright and compact growth habit. Moderate to low vigor and slow growth rate.

*Plant height.*—About 19 cm.

*Lateral branch length.*—About 17 cm.

*Quantity of lateral branches after removal of apical meristem.*—About 3.

*Stem color.*—147D.

*Foliage description.*—Number of leaves per plant: About 40. Number of leaves per lateral branch: About 14. Leaf arrangement: Alternate. Leaf size, fully expanded: Length: About 4.1 cm. Width: About 3.9 cm. Leaf apex: Rounded, apiculate. Leaf base: Acute. Leaf margin: Palmately lobed, 3-lobed. Leaf texture: Abaxial and adaxial surfaces slightly pubescent, smooth and dull. Veins prominent on abaxial surface. Petiole length: About 1.1 cm. Color: Young foliage adaxial surface: 139A. Young foliage abaxial surface: 147B. Fully expanded foliage adaxial surface: 147A. Fully expanded foliage abaxial surface: 147B. Venation abaxial surface: 147C. Venation adaxial surface: 147B. Petiole: 147C.

orescence description:

*Appearance.*—Decorative-type inflorescence form. Inflorescences borne on terminals above foliage, arising from leaf axils. Disc and ray florets arranged acropetally on a flat capitulum.

*Flowering response.*—Under natural conditions, plants flower in the autumn. Inflorescence initiation and development can be induced under short day/long night conditions (at least 13.5 hours of darkness). Plants exposed to 3 or 4 weeks of long day/short night conditions after sticking followed by photoinductive short day/long night conditions, flower about 49 days later.

*Quantity of Inflorescences.*—About 4 inflorescences per flowering stem.

*Inflorescence size.*—Diameter: About 4.8 cm. Depth (height): About 1.8 cm. Diameter of disc: About 1 mm.

*Opening inflorescences.*—Bud shape: Spherical, flattened. Bud size: Length: About 8 mm. Width: About 1 cm. Bud color: 75B.

*Ray florets.*—Shape: Spatulate. Size: Length: About 2.3 cm. Width: About 8 mm. Apex: Emarginate. Base: Acute. Margin: Entire. Texture: Matte, smooth and glabrous. Aspect: Flat. Number of ray florets per inflorescence: About 177. Color: When opening, adaxial surface: 82C. When opening, abaxial surface: 75C. Mature, adaxial surface: 75B. Mature, abaxial surface: 75D. Fading to: 75B.

*Disc florets.*—*Shape: Tubular. Size: Length: About* 4 mm. Width: About 1 mm. Number of disc florets per inflorescence: About 3. Color: Immature: 1C. Mature: 1C.

Peduncle.—Aspect: Strong and angled about 30° to the stem. Length: First peduncle: About 3.5 cm. Fourth peduncle: About 4.5 cm. Texture: Pubescent. Color: 138B.

*Reproductive organs.*—Androecium: Present on disc florets only. Anther color: 9A. Pollen: Moderate. 9A in color. Gynoecium: Present on both ray and disc florets. Style color: 154C.

Disease resistance: No known Chrysanthemum diseases observed to date on plants grown under commercial greenhouse conditions.

Seed Production: Seed production has not been observed.

CHART A

| CHARACTERISTIC | 'SKYLARK' | 'DEBONAIR' |
|---|---|---|
| GROWTH HABIT | Short, compact | Medium |
| GROWTH RATE | Slow | Moderate |
| PLANT HEIGHT | About 19 cm | About 24 cm |
| LATERAL STEM LENGTH | About 17 cm | About 18.5 cm |
| QUANTITY OF LATERAL BRANCHES AFTER PINCHING | About 3 | About 4 |
| STEM COLOR | 147D | 147C |
| LEAF SHAPE | 3-lobed | 5-lobed |
| PETIOLE LENGTH | About 1.1 cm | About 1.5 cm |
| QUANTITY OF INFLORESCENCES PER LATERAL STEM | About 4 | About 5 |
| INFLORESCENCE DIAMETER | About 4.8 cm | About 4.2 cm |
| BUD COLOR | 75B | 65B |
| RAY FLORET LENGTH | About 2.3 cm | About 1.8 cm |
| RAY FLORET WIDTH | About 8 mm | About 5 mm |
| RAY FLORET COLOR, WHEN OPENING, ADAXIAL | 82C | 82D |
| RAY FLORET COLOR, WHEN OPENING, ABAXIAL | 75C | 75D |
| RAY FLORET COLOR, MATURE, ADAXIAL | 75E | 84B |
| RAY FLORET COLOR, MATURE, ABAXIAL | 75D | 76D |
| RAY FLORET COLOR FADING TO | 75B | 84C |
| NUMBER OF RAY FLORETS PER INFLORESCENCE | About 177 | About 196 |
| DISC FLORET COLOR, IMMATURE | 1C | 2B |
| DISC FLORET COLOR, MATURE | 1C | 2B |
| DIAMETER OF DISC | About 1 mm | About 3 mm |
| PEDUNCLE LENGTH, FIRST | About 3.5 cm | About 1.8 cm |
| PEDUNCLE LENGTH, FOURTH | About 4.5 cm | About 3.1 cm |
| PEDUNCLE COLOR | 138B | 137D |
| ANTHER COLOR | 9A | 13B |
| POLLEN COLOR | 9A | 13B |

It is claimed:

1. A new and distinct cultivar of Chrysanthemum plant named 'Skylark', as illustrated and described.

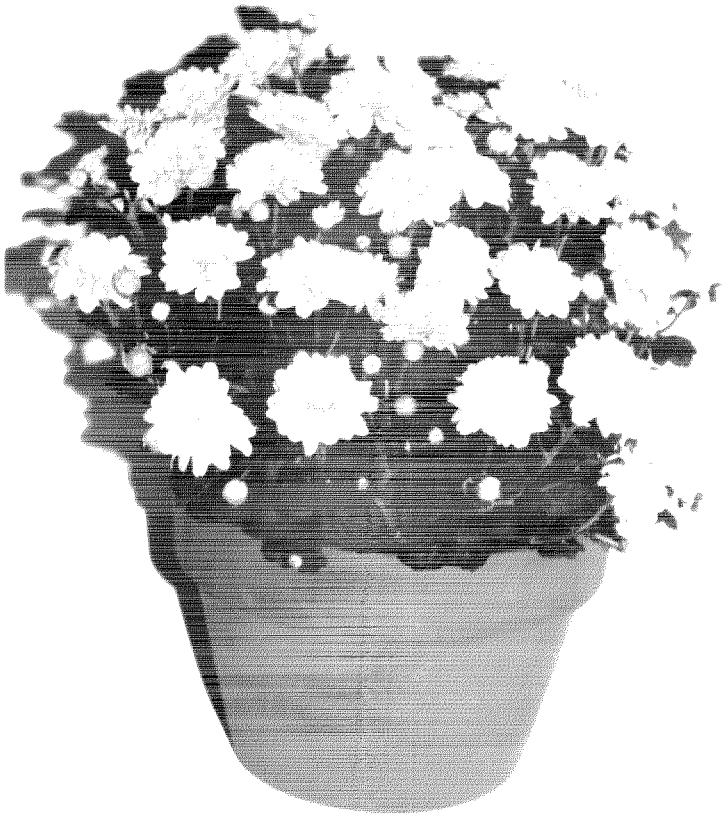

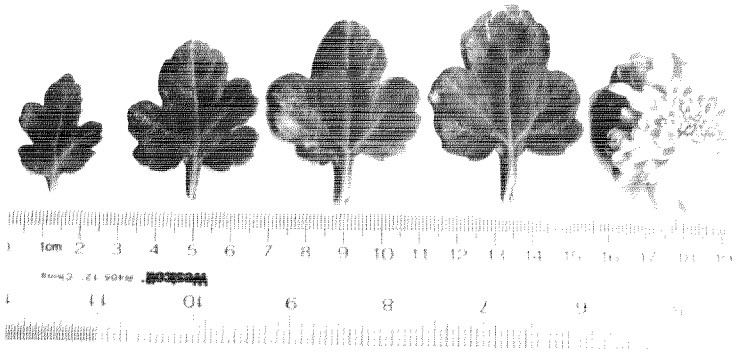

* * * * *